United States Patent [19]

Döbeli et al.

[11] Patent Number: 4,877,830

[45] Date of Patent: Oct. 31, 1989

[54] METAL CHELATE RESINS

[75] Inventors: Heinz Döbeli, Ziefen; Frich Hochuli, Arisdorf, both of Switzerland

[73] Assignee: Hoffmann-La Roche Inc., Nutley, N.J.

[21] Appl. No.: 72,452

[22] Filed: Jul. 13, 1987

[51] Int. Cl.$^4$ .................... C07C 101/24; C07K 3/20; B01J 20/32
[52] U.S. Cl. .................... 525/54.3; 525/54.31; 525/54.32; 525/54.4; 525/54.45
[58] Field of Search .................... 525/54.1, 54.3, 54.31, 525/54.32, 54.4, 54.45

[56] References Cited

U.S. PATENT DOCUMENTS 4,626,416 12/1986 DeVoe et al. .................... 525/54.1

FOREIGN PATENT DOCUMENTS 0253303 1/1988 European Pat. Off. .

OTHER PUBLICATIONS

Biol. Chem. Hoppe-Seyler, vol. 368, No. 7, Jul. 1987, p. 748.
Dobeli et al., "New Nickel Chelate resins-useful for Protein Purification by Affinity Chromatography", Switzerland 86-002782 Abstract only.

*Primary Examiner*—John Kight
*Assistant Examiner*—Nathan M. Nutter
*Attorney, Agent, or Firm*—Jon S. Saxe; George M. Gould; Julie M. Prlina

[57] ABSTRACT

Metal chelate resins whose complexed nitrilotriacetic acid residues are bound to a carrier matrix via a spacer and which are suitable for metal chelate chromatography of proteins, especially those which contain neighboring histidines.

6 Claims, No Drawings

METAL CHELATE RESINS

Metal chelate affinity chromatography, a new purification method for proteins, was introduced in 1975 by Porath et al. [Nature 258, 598-599 (1975)]. This new technology has meanwhile been used successfully in many places and has already been discussed in review articles [Lëonnerdal, B. and Keen C. L., J. Appl. Biochem. 4, 203-208 (1982); Sulkowski, E., Trends in Biotechnology 3, 1-7 (1985)]. Metal chelate affinity chromatography is based on the discovery that metal ions such as $Cu^{2+}$ and $Zn^{2+}$ bound (immobilized) to a chromatography gel by chelate bonding can take part in a reversible interaction with electron donor groups situated on the surface of proteins, especially the imidazole side-chain of histidine. At a pH value at which the electron donor group is present at least partially in nonprotonized form the protein is bonded to the chromatography gel (e.g. agarose) and can subsequently be eluted by means of a buffer with a lower pH value at which the electron donor group is protonized. Iminodiacetic acid, which is bound to the carrier matrix of the resin via a so-called spacer, has, for example, been very reliable as the chelate former.

An ideal chelate resin for the purification of biopolymers must therefore on the one hand strongly complex the metal ions and on the other hand must permit reversible interactions between metal ions and proteins. Immobilized iminodiacetic acid largely fulfils these requirements for $Cu^{II}$ ions, but only to a limited extent for $Ni^{II}$ ions, since the latter are only weakly bonded and are often washed-out even upon loading with the protein mixture. On the other hand, $Ni^{II}$ chelate resins are of particular interest for the purification of biological material, as $Ni^{2+}$ has a high coordination number: $Ni^{II}$ ions complex six ligands, $Cu^{II}$ ions preferably complex four. In nickel complexes four valencies are available for anchoring the metal ions in the resin and two valencies are available for the interchanges between metal ions and biopolymers.

Hitherto there has not been a lack of attempts to manufacture chelate resins with a possible greater affinity to a metal ion. As complex forming components there have been used e.g. N,N,N'-ethylenediaminetriacetic acid [Haner, M. et al., anal. Biochem. 138, 229-234 (1984)] and 1,3-diaminopropane N,N,N',N'-tetraacetic acid [Moyers, E. M. and J. S. Fritz, Anal. Chem. 49, 418-423 (1977)]. However these resins have the disadvantage that the interchanges between metal ions and biopolymers are not optimal.

SUMMARY OF THE INVENTION

The present invention is concerned with novel resins, which are suitable for metal chelate chromatography, and their manufacture as well as the use of these metal chelate resins for the purification of proteins, especially those which contain neighbouring histidine residues.

DETAILED DESCRIPTION

Nitrilotriacetic acid is a four-pronged chelate former. Immmobilized nitrilotriacetic acid would be a suitable chelate resin for metal ions with the coordination number six, since two valencies are available for the reversible bonding of the biopolymers. Such a metal chelate resin should be especially suitable for the binding of proteins with two neighbouring histidines on its surface.

Nitrilotriacetic acid can, however, not be bound to a carrier analogously to iminodiacetic acid without substantially diminishing its capability of chelate formation. This problem can be solved by the manufacture of novel nitrilotriacetic acid derivatives of the formula $$NH_2-(CH_2)_x-CH(COOH)-N(CH_2COOH)_2 \quad I$$

wherein x signifies 2, 3 or 4, and their immobilization on a carrier matrix via a spacer.

The present invention is therefore concerned with nitrilotriacetic acid derivatives of the previously mentioned formula and their salts as well as a process for their manufacture. Especially preferred nitrilotriacetic acid derivatives in accordance with the invention are N-[3-amino-1-carboxypropyl]-iminodiacetic acid and N-[5-amino-1-carboxypentyl]-iminodiacetic acid.

The present invention is also concerned with metal chelate resins which are suitable, on the basis of their metal chelate groups, for the purification of proteins, especially those which contain neighbouring histidines, as well as a process for their manufacture.

The metal chelate resins in accordance with the invention are defined by the general formula Carrier matrix-spacer-$NH-(CH_2)_x-CH(COOH)-N(CH_2COO^-)_2$ $Ni^{2+}$, wherein x signifies 2, 3 or 4.

As the carrier matrix there come into consideration materials which are used in affinity and gel chromatography, for example cross-linked dextrans, agarose (especially in the form known under the trade names Sepharose ®, Pharmacia, Uppsala, Sweden) or polyacrylamides.

As the spacer there come into consideration the spacer groups already known from affinity chromatography, with the groups $-O-CH_2-CH(OH)-CH_2-$ and $-O-CO-$ being preferred.

Especially preferred chelate resins in accordance with the invention are those of the formulae

[Agarose or Sepharose ® CL 6B]$-O-CH_2-CH(OH)-CH_2-NH-(CH_2)_4-CH(COOH)-N(CH_2COO^-)_2Ni^{2+}$ and Agarose$-O-CO-NH-(CH_2)_2-CH(COOH)-N(CH_2COO^-)_2Ni^{2+}$.

The manufacture of the nitrilotriacetic acid derivatives in accordance with the invention can be effected in a manner known per se by reacting a N-terminal protected compound of the formula $R-HN-(CH_2)_x-CH(NH_2)-COOH$, wherein R signifies an amino protecting group and x signifies 2, 3 or 4, with bromoacetic acid in an alkaline medium and subsequently cleaving off the protecting group. A preferred amino protecting group is the benzyloxycarbonyl residue (Z), which can be removed by catalytic hydrogenation, preferably with Pd/C. In this manner $N^\gamma$-Z-L-2,4-diaminobutyric acid and $N^\epsilon$-Z-L-lysican be converted into the previously mentioned especially preferred nitrilotriacetic acid derivatives.

The manufacture of the chelate resins in accordance with the invention can be effected in a manner known per se, whereby firstly the carrier matrix is functionalized (introduction of the spacer) and then the desired nitrilotriacetic acid derivative is covalently bonded to the spacer.

When agarose is used as the carrier matrix it is reacted, for example, with epibromohydrin in an alkaline medium so that there is obtained oxirane-agarose which contains

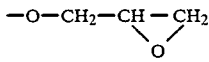

groups. The oxirane-agarose can then be converted into the desired chelate resin in accordance with the invention in a manner known per se by reaction with a nitriloacetic acid derivative in accordance with the invention, preferably with N-[3-amino-1-carboxypropyl]-iminodiacetic acid or N-[5-amino-1-carboxypentyl]-iminodiacetic acid, in an alkaline medium and subsequent washing with a nickel salt solution, for example with nickel sulphate. In special cases the use of a different metal ion (e.g. Co, Cd) is advantageous, so the corresponding metal chelate can be obtained readily by reacting the resin with a suitable metal salt. Epichlorohydrin can also be used in place of epibromohydrin. As the agarose there is conveniently used a standardized product, preferably Sepharose® from the firm Pharmacia, Uppsala, Sweden. Sepharose® Cl-6B is especially suitable. In an analogous manner, polyacrylamide resins which contain free hydroxy groups can be converted into chelate resins in accordance with the invention as previously indicated. When cation exchange resins are used as the matrix, the coupling of the nitrilotriacetic acid derivative can be effected directly with the formation of an amide bond.

For the manufacture of the chelate resins in accordance with the invention there can also be used commercially available, already functionalized carrier matrices. An especially preferred functionalized carrier matrix in connection with the present invention is imidazolecarbamate-agarose which contains

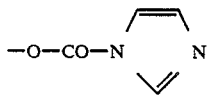

groups and which is marketed under the trade mark Reactigel ™ of the firm Pierce, Rockford, IL, USA.

It has been shown that the chelate resins in accordance with the invention are distinguished by an especially high specificity towards peptides and proteins which contain neighbouring histidine residues and are therefore especially suitable for the purification of proteins with neighbouring histidine residues, especially those which contain 2 neighbouring histidine residues. The term "neighbouring histidine residues" refers to the arrangement of the histidine residues of the particular peptides and proteins in three dimensional space, i.e. on the surface of the compounds. The neighbourhood of the histidine residues can be given already on the basis of the primary structure or can be realized only by the secondary and/or tertiary structure. The chelate resins in accordance with the invention are accordingly suitable for the purification of native and denatured proteins which contain several, especially neighbouring, preferably immediately neighbouring, histidine residues.

The chelate resins in accordance with the invention can be used batch-wise or continuously in operating columns. Prior to the loading with protein the chelate resins in accordance with the invention are conveniently equilibrated with an aqueous buffer which itself does not form chelates with nickel, preferably a phosphate buffer, pH 8. The equilibrating buffer (as well as the elution buffer) can contain a denaturing agent or a detergent, for example guanidine.HCl, urea or Triton. The addition of such a denaturing agent or detergent permits problem-free operations even with proteins which are extremely difficultly soluble in aqueous solution such as, for example, membrane proteins. The elution of the protein can be carried out at a constant pH value or with linear or discontinuously falling pH gradients. The optimal elution conditions depend on the amount and type of impurities present, the amount of material to be purified, the column dimensions etc. and are conveniently determined on a case by case basis.

The following Examples illustrate the manufacture of nitrilotriacetic acid derivatives in accordance with the invention as well as the manufacture of metal chelate resins in accordance with the invention and their use in the purification of proteins with neighbouring histidine residues.

EXAMPLE 1

41.7 g of bromoacetic acid were dissolved in 150 ml of 2N sodium hydroxide solution and cooled to 0° C. Thereto there was slowly added dropwise at 0° C. while stirring a solution of 42 g of $N^\epsilon$-Z-L-lysine in 225 ml of 2N sodium hydroxide solution. After 2 hours the cooling was removed and the mixture was stirred overnight. The reaction mixture was then held at 50° C. for 2 hours and 540 ml of 1N hydrochloric acid were subsequently added. After the mixture had been cooled the separated crystals were filtered off. The product was dissolved in 1N sodium hydroxide solution and again precipitated with the same amount of 1N hydrochloric acid and filtered off. There were obtained 40 g of N-[5-benzyloxycarbonylamino-1-carboxypentyl]-iminodiacetic acid in the form of white crystals, m.p. 172°–174° C. (dec.), $[\alpha]_D = +9.9°$ (c=1; 0.1N NaOH).

7.9 g of the lysine derivative obtained were dissolved in 49 ml of 1N sodium hydroxide solution and, after the addition of a spatula tip of 5% Pd/C, hydrogenated at room temperature and normal pressure. The catalyst was filtered off and the filtrate was evaporated. There resulted 6.2 g of N-[5-amino-1-carboxypentyl]-iminodiacetic acid whose structure, $NH_2—(CH_2)_4—CH(COOH)—N—(CH_2COOH)_2$, was confirmed by the NMR spectrum.

100 ml of Sepharose® CL-6B (Pharmacia) were washed twice on a glass suction filter with about 500 ml of water and then reacted at 30° C. for 4 hours in a 500 ml round flask with 16 ml of 4N sodium hydroxide solution and 8.22 ml of epibromohydrin. The total volume of the reaction mixture was 200 ml. The activated Sepharose was subsequently filtered off, washed neutral with water and transferred back into the reaction vessel. 6.5 g of N-[5-amino-1-carboxypentyl]-iminodiacetic acid were dissolved in 50 ml of water and added to the activated Sepharose together with 10.6 g of solid sodium carbonate. The mixture was stirred slowly at 60° C. overnight. The resulting chelate resin with the formula [Sepharose® CL-6B]—O—CH$_2$—CH(OH)—CH$_2$—NH—(CH$_2$)$_4$—CH(COOH)—N(CH$_2$COOH)$_2$ (NTA resin) was subsequently washed in a chromatography column in succession with 500 ml of water, 100 ml of aqueous NiSO$_4$·6H$_2$O (2 wt.%), 200 ml of water, 200 ml of 0.2M acetic acid (containing 0.2M NaCl and 0.1 wt./vol.% Tween 20) and 200 ml of water. The nickel ion concentration in the resulting chelate resin of the formula [Sepharose ® CL-6B]—O—CH$_2$—CH(OH)—CH$_2$—NH—(CH$_2$)$_4$—CH(COOH)—N(CH$_2$COO$^-$)$_2$Ni$^{2+}$ amounted to about 7.1 micromol/ml.

EXAMPLE 2

For a qualitative comparison of the stabilities of the nickel complexes of immobilized iminodiacetic acid (IMA) and imobilized nitrilotriacetic acid (NTA), the two nickel chelate resins were eluted with an aqueous solution of iminodiacetic acid and the washing out of the nickel ions was followed.

50 ml of IMA resin of the formula Agarose—O—CH$_2$—CH(OH)—CH$_2$—N(CH$_2$COOH)$_2$ (preparation see European Patent Application No. 84101814.6, Publication No. 118 808) were placed in a chromatography column (d=1.6 cm) and washed well with water. Then, 10 ml of a 0.012M NiSO$_4$·5H$_2$O solution in water were introduced at a flow rate of 100 ml/h and the column was subsequently washed with 70 ml of water. It was eluted with 0.1M aqueous iminodiacetic acid (IMA), pH 7.0. 10 ml fractions were collected. Nickel ions could be detected (UV 390 nm) in fractions 10–19.

In the same manner, 50 ml of NTA resin of the structure [Sepharose ® CL-6B]—O—CH$_2$—CH(OH)—CH$_2$—NH—(CH$_2$)$_4$—CH(COOH)—N(CH$_2$COOH)$_2$ were placed in a chromatography column (d=1.6 cm), washed with water, thereafter loaded with 10 ml of 0.012M NiSO$_4$·5H$_2$O, again washed with water and eluted with 0.1M aqueous iminodiacetic acid, pH 7.0. Nickel ions could only be detected (UV 390 nm) in fractions 30–34, from which it is evident that the Ni$^{II}$ ions are bound more strongly in the novel NTA resin than in the known IMA resin.

EXAMPLE 3

6.5 g of bromoacetic acid were dissolved in 8.1 ml of 4N sodium hydroxide solution and cooled to 0° C. Thereto there was added dropwise while stirring a solution of 4.9 g of N$^\gamma$-benzyloxycarbonyl-L-2,4-diaminobutyric acid in 24.4 ml of 2N sodium hydroxide solution. After 2 hours the cooling was removed and the mixture was stirred overnight. The reaction mixture was then held at 50° C. for 2 hours and 12.2. ml of 4N hydrochloric acid were subsequently added. After the mixture had been cooled the separated crystals were filtered off. The product was dissolved in 2N sodium hydroxide solution and again precipitated with 6.1 ml of 4N hydrochloric acid and filtered off. There were obtained 5 g of N-[3-benzyloxycarbonylamino-1-carboxypropyl]-iminodiacetic acid in the form of white crystals, m.p. 136°–138° C. (dec.).

2.9 g of the butyric acid derivative obtained were dissolved in 16 ml of 1N sodium hydroxide solution and, after the addition of a spatula tip of 5% Pd/C, hydrogenated at room temperature and normal pressure. The catalyst was filtered off and the filtrate was evaporated. There resulted 2.2 g of N-[3-amino-1-carboxypropyl]-iminodiacetic acid whose structure, NH$_2$—(CH$_2$)$_2$—CH(COOH)—N(CH$_2$COOH)$_2$, was confirmed by the NMR spectrum.

A solution of 1.9 g of the N-[3-amino-1-carboxypropyl]-iminodiacetic acid obtained in 50 ml of water was treated with 2.6 g of solid sodium carbonate. To the mixture, cooled to 0° C., were added 50 ml of agarose activated with imidazolecarbamate (Reacti-Gel TM of the firm Pierce). After incubation at 0° C. for 15 hours the resulting chelate resin of the formula Agrose—O—CO—NH—(CH$_2$)$_2$—CH(COOH)—N(CH$_2$COOH)$_2$ was filtered off, washed with water and loaded with Ni$^{II}$ ions as described in Example 1. The nickel ion concentration in the resulting chelate resin of the formula Agarose—O—CO—NH—(CH$_2$)$_2$—CH(COOH)—N(CH$_2$COO$^-$)Ni$^{2+}$ amounted to 3.1 micromol/ml.

EXAMPLE 4

A column ($\phi$ 1 cm, length=4.8 cm) was filled with metal-free chelate resin of the formula [Sepharose ® CL-6B]—O—CH$_2$—CH(OH)—CH$_2$—NH—(CH$_2$)$_4$—CH(COOH)—N(CH$_2$COOH)$_2$ (NTA resin) and the resin was brought into the nickel form by rinsing with a three-fold column volume of 0.1M NiSO$_4$·5H$_2$O and subsequently washing with a three-fold columnn volume of 0.2M acetic acid. It was subsequently equilibrated with 0.1M sodium phosphate buffer (pH 8.0) and 0.5 NaCl (flow in each case 13.2 ml/hr.).

1 mg of a model peptide of the formula His-His-Leu-Gly-Gly-Ala-Lys-Glu-Ala-Gly-Asp-Val was taken up in 1 ml of equilibration buffer and applied on to the column. The model peptide could be eluted by washing with 0.2M imidazole in 0.1M sodium phosphate, pH 8.0, and 0.5M NaCl. The detection in the eluate was effected with ninhydrin according Moore, S. and Stein, W. [J. Biol. Chem. 176, 367–388 (1948)].

EXAMPLE 5

In a manner analogous to Example 4, a column ($\phi$=1 cm, length=4.8 cm) was filled with NTA resin and the resin was brought into the nickel form. After washing with 0.2M acetic acid the column was equilibrated with 7M guanidine·HCl in 0.1M sodium phosphate buffer (pH 8.0).

Different amounts (up to 12.7 mg) of a model peptide with the formula Asp-Arg-Val-Tyr-Ile-His-Pro-Phe-His-Leu-Val-Ile-His-Ser were dissolved in 1 ml of 7M guanidine·HCl and 0.1M sodium phosphate (pH 8.0) and applied on to the column. This peptide is very well soluble in 7M guanidine·HCl, but is poorly soluble in 0.1M sodium phosphate and 0.5M NaCl. The elution was effected by lowering the pH value stepwise. The peptide was detected by means of UV spectrometry at $\lambda$=280 nm.

Trypsin from bovine pancreas and cytochrome C from horse heart were used as comparative substances. Neither of the two proteins bonded to the NTA resin at pH 8. Obviously the arrangement of the histidines plays a decisive role. In the case of trypsin three histidines are situated in positions 29, 46 and 79, which in spite of the breaking of the stucture by 7M guanidine are not in the position to form a stable complex and in the case of cytochem C the two histidines are indeed spacially neighbouring (positions 18 and 26), but are not in the position to form a two-pronged ligand, since one histidine is bonded to the haem-iron.

EXAMPLE 6

Lactate dehydrogenase isoenzymes are tetrameric proteins with a molecular weight of 140,000. The isoenzymes from hogs are largely homologous with the exception of the amino terminal region. This is situated on the protein surface. The heart type isoenzyme has no histidine in this region, but the muscle type has three, among them the sequence His-Val-Pro-His [L. Li et al., J. Biol. Chem. 258, 7029–7032 (1983)].

As described in Example 4, a column ($\phi$=1 cm, length=4.8 cm) was filled with NTA resin, the resin was brought into the nickel form and equilibrated with 0.1M sodium phosphate buffer (pH 7.5) and 0.5M NaCl. 2 mg of lactate dehydrogenase from hog heart ($H_4$-LOH) or hog muscle ($M_4$-LOH) were taken up in 1.5 ml of equilibration buffer and applied to the column. While $H_4$-LOH was not adsorbed in spite of its 28 histidine residues, $M_4$-LOH was adsorbed at pH 7.5 and could be eluted by lowering the pH value to 6.

This experiment shows that the NTA resin is extremely selective for proteins which have as a structural element neighbouring histidines on the protein surface.

We claim:

1. A metal chelate resin of the formula:

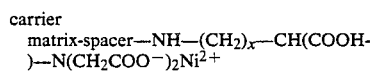

wherein X=2–4.

2. The metal chelate resin of claim 1 wherein the carrier matrix is cross-linked agarose.

3. The metal chelate resin of claim 2 wherein the spacer is —O—CO—.

4. A method for the manufacture of a metal chelate resin comprising the steps of:
   a) reacting a carrier matrix with a spacer;
   b) reacting the carrier matrix-spacer complex with a compound of the formula:

wherein X=2–4; and
   c) washing with a nickel salt solution.

5. The method of claim 8, wherein the carrier matrix-spacer complex is oxirane-agarose which contains

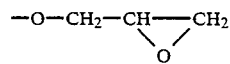

groups.

6. The method of claim 8 wherein the fuctionalized carrier matrix-spacer complex is imidazolecarbamate-agarose which contains

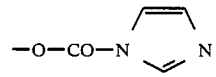

groups.

* * * * *

UNITED STATES PATENT AND TRADEMARK OFFICE
CERTIFICATE OF CORRECTION

PATENT NO. : 4,877,830

DATED : October 31, 1989

INVENTOR(S) : Heinz Dobeli & Erich Hochuli

It is certified that error appears in the above-identified patent and that said Letters Patent is hereby corrected as shown below:

Column 8, Claim 5, line 11, delete "Claim 8" and insert --Claim 4--.

Column 8, Claim 6, line 19, delete "Claim 8" and insert --Claim 4--.

Signed and Sealed this

Sixth Day of November, 1990

Attest:

HARRY F. MANBECK, JR.

Attesting Officer

Commissioner of Patents and Trademarks